(12) United States Patent
Tegels et al.

(10) Patent No.: US 9,883,855 B2
(45) Date of Patent: Feb. 6, 2018

(54) APPARATUS AND METHOD FOR HEART VALVE REPAIR

(71) Applicant: St. Jude Medical, LLC, Abbott Park, IL (US)

(72) Inventors: Zachary J. Tegels, Minneapolis, MN (US); John W. Ibeling, Otsego, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 596 days.

(21) Appl. No.: 14/374,741

(22) PCT Filed: Jan. 25, 2013

(86) PCT No.: PCT/US2013/023082
§ 371 (c)(1),
(2) Date: Jul. 25, 2014

(87) PCT Pub. No.: WO2013/112797
PCT Pub. Date: Aug. 1, 2013

(65) Prior Publication Data
US 2015/0038988 A1 Feb. 5, 2015

Related U.S. Application Data

(60) Provisional application No. 61/590,557, filed on Jan. 25, 2012.

(51) Int. Cl.
*A61B 17/10* (2006.01)
*A61B 17/00* (2006.01)
(Continued)

(52) U.S. Cl.
CPC .. *A61B 17/00234* (2013.01); *A61B 17/00491* (2013.01); *A61B 17/0467* (2013.01);
(Continued)

(58) Field of Classification Search
CPC ........ A61B 17/00234; A61B 17/00491; A61B 17/0218; A61B 17/0467; A61B 17/0469;
(Continued)

(56) References Cited

U.S. PATENT DOCUMENTS 5,041,129 A   8/1991  Hayhurst et al.
5,156,608 A   10/1992 Troidl et al.
(Continued)

FOREIGN PATENT DOCUMENTS

AU   2002300522 B2   1/2007
WO      9620749 A1   7/1996
(Continued)

OTHER PUBLICATIONS

International Preliminary Report on Patentability for Application No. PCT/US2012/023437 dated Aug. 6, 2013.
(Continued)

*Primary Examiner* — Katherine M Shi
(74) *Attorney, Agent, or Firm* — Lerner, David, Littenberg, Krumholz & Mentlik, LLP

(57) ABSTRACT

A device 10 for gathering tissue of a heart valve leaflet 2 may include an outer tube 16 extending in an elongation direction, a capture tool 22 moveable in the outer tube between a contained position and a use position, and a tissue securing component 32 disposed at a distal end 17 of the outer tube and adapted to be applied to tissue 8 captured by the capture tool to hold the captured tissue in a gathered configuration. The capture tool may include a first element 20 and a second element 22 that are moveable relative to one another in the elongation direction. The first and second elements 20, 22 may be operable to capture tissue 8 of the heart valve leaflet 2 therebetween and to draw the captured tissue into the outer tube 16 in the gathered configuration.

14 Claims, 5 Drawing Sheets

(51) Int. Cl.

| | | |
|---|---|---|
| *A61B 17/04* | (2006.01) | |
| *A61B 17/068* | (2006.01) | |
| *A61B 17/29* | (2006.01) | |
| *A61B 17/128* | (2006.01) | |
| *A61B 17/221* | (2006.01) | |
| *A61B 17/064* | (2006.01) | |
| *A61B 17/12* | (2006.01) | |
| *A61B 17/22* | (2006.01) | |
| *A61B 17/02* | (2006.01) | |

(52) U.S. Cl.
CPC ........ *A61B 17/0469* (2013.01); *A61B 17/068* (2013.01); *A61B 17/1285* (2013.01); *A61B 17/29* (2013.01); *A61B 17/0218* (2013.01); *A61B 17/221* (2013.01); *A61B 2017/00243* (2013.01); *A61B 2017/00349* (2013.01); *A61B 2017/00353* (2013.01); *A61B 2017/00358* (2013.01); *A61B 2017/00539* (2013.01); *A61B 2017/00783* (2013.01); *A61B 2017/00858* (2013.01); *A61B 2017/00862* (2013.01); *A61B 2017/00867* (2013.01); *A61B 2017/00951* (2013.01); *A61B 2017/00986* (2013.01); *A61B 2017/0417* (2013.01); *A61B 2017/0464* (2013.01); *A61B 2017/0645* (2013.01); *A61B 2017/12018* (2013.01); *A61B 2017/22069* (2013.01); *A61B 2017/292* (2013.01)

(58) Field of Classification Search
CPC . A61B 17/068; A61B 17/1285; A61B 17/221; A61B 17/29; A61B 2017/00243; A61B 2017/00349; A61B 2017/00353; A61B 2017/00358; A61B 2017/007; A61B 17/12009
USPC ................ 606/113, 139, 142, 144, 151, 216
See application file for complete search history.

(56) References Cited

U.S. PATENT DOCUMENTS

| | | | |
|---|---|---|---|
| 5,499,991 | A | 3/1996 | Garman et al. |
| 5,601,573 | A | 2/1997 | Fogelberg et al. |
| 5,741,278 | A | 4/1998 | Stevens |
| 5,749,879 | A | 5/1998 | Middleman et al. |
| 5,921,993 | A | 7/1999 | Yoon |
| 6,258,105 | B1 | 7/2001 | Hart et al. |
| 6,440,152 | B1 | 8/2002 | Gainor et al. |
| 6,569,182 | B1 | 5/2003 | Balceta et al. |
| 6,626,930 | B1 | 9/2003 | Allen et al. |
| 6,752,813 | B2 | 6/2004 | Goldfarb et al. |
| 6,945,978 | B1 | 9/2005 | Hyde |
| 7,011,669 | B2 | 3/2006 | Kimblad |
| 7,464,712 | B2 | 12/2008 | Oz et al. |
| 7,569,062 | B1 | 8/2009 | Kuehn et al. |
| 7,758,595 | B2 | 7/2010 | Allen et al. |
| 8,777,966 | B2 | 7/2014 | Dale et al. |
| 8,951,285 | B2 | 2/2015 | Sugimoto et al. |
| 2001/0016750 | A1 | 8/2001 | Malecki et al. |
| 2002/0010388 | A1 | 1/2002 | Taylor et al. |
| 2002/0013571 | A1 | 1/2002 | Goldfarb et al. |
| 2002/0035390 | A1 | 3/2002 | Schaldach et al. |
| 2002/0049457 | A1 | 4/2002 | Kaplan et al. |
| 2002/0107531 | A1 | 8/2002 | Schreck et al. |
| 2002/0183768 | A1 | 12/2002 | Deem et al. |
| 2003/0065335 | A1 | 4/2003 | Guido et al. |
| 2003/0093071 | A1 | 5/2003 | Hauck et al. |
| 2003/0120264 | A1 | 6/2003 | Lattouf |
| 2004/0030335 | A1 | 2/2004 | Zenati et al. |
| 2004/0039442 | A1 | 2/2004 | St. Goar et al. |
| 2004/0087985 | A1 | 5/2004 | Loshakove et al. |
| 2004/0176784 | A1 | 9/2004 | Okada |
| 2004/0181238 | A1 | 9/2004 | Zarbatany et al. |
| 2004/0193185 | A1 | 9/2004 | McBrayer |
| 2005/0004583 | A1 | 1/2005 | Oz et al. |
| 2005/0090837 | A1 | 4/2005 | Sixto et al. |
| 2005/0096671 | A1 | 5/2005 | Wellman et al. |
| 2005/0107871 | A1 | 5/2005 | Realyvasquez et al. |
| 2005/0125011 | A1 | 6/2005 | Spence et al. |
| 2005/0143763 | A1 | 6/2005 | Ortiz et al. |
| 2005/0149072 | A1 | 7/2005 | DeVries et al. |
| 2005/0177176 | A1 | 8/2005 | Gerbi et al. |
| 2005/0251161 | A1 | 11/2005 | Saadat et al. |
| 2006/0009800 | A1 | 1/2006 | Christianson et al. |
| 2006/0089671 | A1 | 4/2006 | Goldfarb et al. |
| 2006/0122633 | A1 | 6/2006 | To et al. |
| 2006/0173422 | A1 | 8/2006 | Reydel et al. |
| 2006/0173473 | A1 | 8/2006 | Bob |
| 2007/0049952 | A1* | 3/2007 | Weiss ................ A61B 17/0218 606/144 |
| 2007/0093857 | A1 | 4/2007 | Rogers et al. |
| 2007/0102474 | A1 | 5/2007 | Shelton et al. |
| 2007/0102475 | A1 | 5/2007 | Ortiz et al. |
| 2007/0142846 | A1 | 6/2007 | Catanese et al. |
| 2007/0162056 | A1 | 7/2007 | Gerbi et al. |
| 2007/0197858 | A1 | 8/2007 | Goldfarb et al. |
| 2007/0198032 | A1 | 8/2007 | Ortiz |
| 2007/0225734 | A1 | 9/2007 | Bell et al. |
| 2008/0125796 | A1 | 5/2008 | Graham |
| 2008/0234705 | A1 | 9/2008 | Cropper et al. |
| 2008/0255427 | A1 | 10/2008 | Satake et al. |
| 2008/0294175 | A1* | 11/2008 | Bardsley .......... A61B 17/12009 606/113 |
| 2008/0300624 | A1 | 12/2008 | Schwemberger et al. |
| 2008/0319455 | A1 | 12/2008 | Harris et al. |
| 2009/0062852 | A1 | 3/2009 | Marino |
| 2009/0118744 | A1 | 5/2009 | Wells et al. |
| 2009/0125038 | A1 | 5/2009 | Ewers et al. |
| 2009/0149870 | A1 | 6/2009 | Jugenheimer et al. |
| 2011/0054521 | A1 | 3/2011 | Ventura et al. |
| 2011/0077668 | A1 | 3/2011 | Gordon et al. |
| 2011/0087242 | A1 | 4/2011 | Pribanic et al. |
| 2011/0114700 | A1 | 5/2011 | Baxter, III et al. |
| 2011/0230897 | A1 | 9/2011 | Palermo et al. |
| 2011/0313432 | A1 | 12/2011 | Miles et al. |
| 2012/0022532 | A1 | 1/2012 | Garrison |
| 2012/0109159 | A1 | 5/2012 | Jordan et al. |
| 2012/0226291 | A1 | 9/2012 | Malizia et al. |
| 2013/0046332 | A1 | 2/2013 | Jones et al. |
| 2014/0039607 | A1 | 2/2014 | Kovach |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 2002000121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |
| WO | 2013019415 A1 | 2/2013 |
| WO | 2013116617 A1 | 8/2013 |
| WO | 2014022464 A1 | 2/2014 |

OTHER PUBLICATIONS

International Search Report and Written Opinion for Application No. PCT/US2013/023082 dated Oct. 1, 2013.
International Search Report and Written Opinion for Application No. PCT/US2013/024304 dated Jul. 5, 2013.
International Search Report and Written Opinion for Application No. PCT/US2013/052822 dated Jan. 21, 2014.

(56) References Cited

OTHER PUBLICATIONS

International Search Report and Written Opinion for Application No. PCT/US2013/052838 dated Oct. 11, 2013.
International Search Report and Written Opinion for Application No. PCT/US2013/052843 dated Oct. 11, 2013.
International Search Report and Written Opinion for Application No. PCT/US2013/065360 dated Apr. 23, 2014.
International Search Report for Application No. PCT/US2012/023437 dated Apr. 24, 2012.
International Search Report for Application No. PCT/US2013/023077 dated May 14, 2013.
International Search Report for Application No. PCT/US2013/052832 dated Jan. 15, 2014.

* cited by examiner

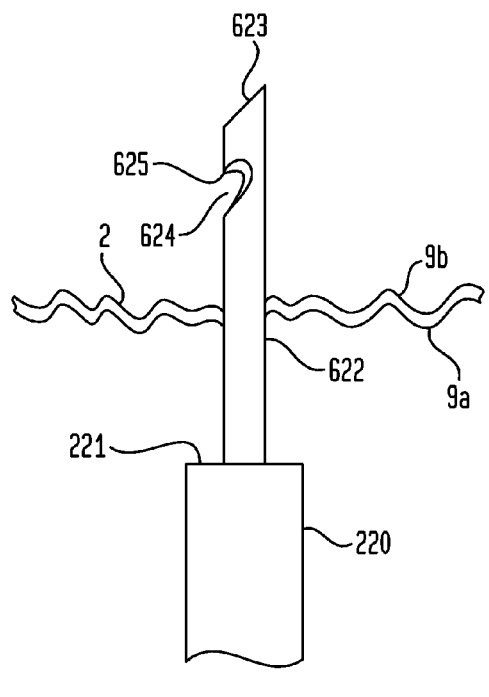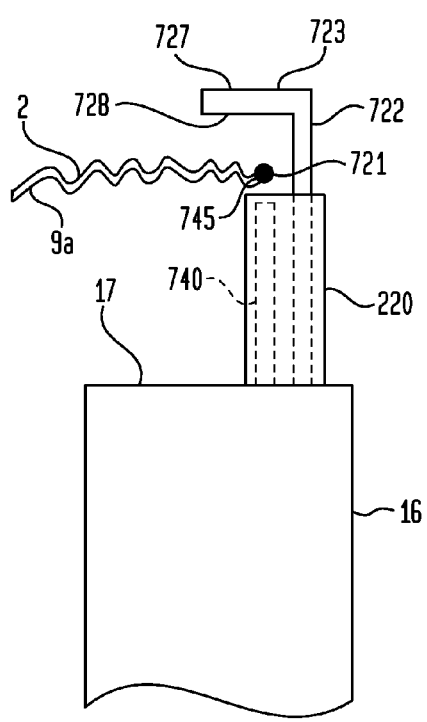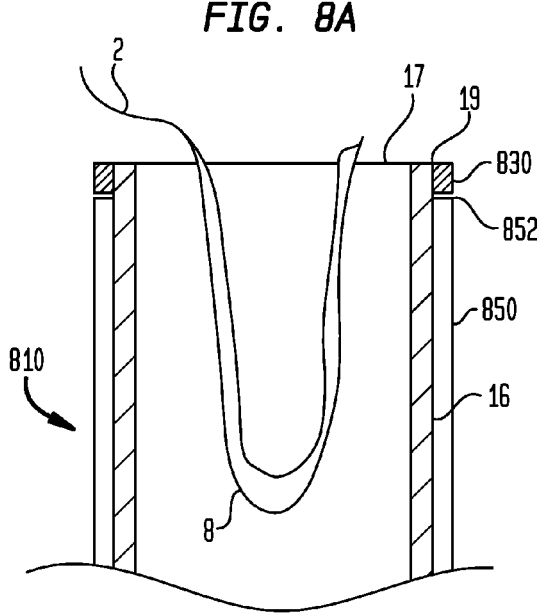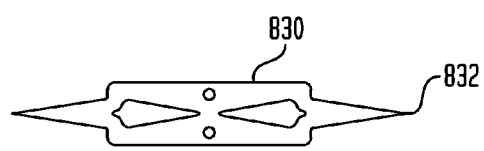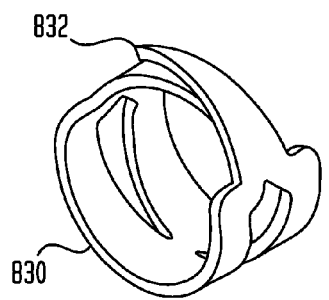

APPARATUS AND METHOD FOR HEART VALVE REPAIR

CROSS-REFERENCE TO RELATED APPLICATION

This application is a national phase entry under 35 U.S.C. § 371 of International Application No. PCT/US2013/023082 filed Jan. 25, 2013, published in English, which claims the benefit of the filing date of U.S. Provisional Patent Application No. 61/590,557 filed Jan. 25, 2012, the disclosures of which are hereby incorporated by reference herein.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be broken. As a result, the valve does not close normally, and the unsupported valve leaflet may bulge back, or "prolapse," into the left atrium like a parachute. Thus, as the ventricle contracts, the abnormal leaflet may be propelled backwards, beyond its normal closure line into the left atrium, thereby allowing blood to flow back into the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

Devices and methods for gathering of heart valve leaflet tissue are disclosed. A device for gathering tissue of a heart valve leaflet may include an outer tube extending in an elongation direction, a capture tool moveable in the outer tube between a contained position and a use position, and a tissue securing component disposed at a distal end of the outer tube and adapted to be applied to captured heart valve leaflet tissue to hold the captured tissue in a gathered configuration. The capture tool may include a first element and a second element that are moveable relative to one another in the elongation direction. The first and second elements may be operable to capture tissue therebetween and to draw the captured tissue into the outer tube in the gathered configuration.

The first element may include a containment tube having a proximal portion and a distal portion. The containment tube may be moveable between a containment tube retracted position in which the distal portion of the containment tube lies within the outer tube, and a containment tube deployed position in which the proximal portion of the containment tube extends substantially in a linear direction and the distal portion of the containment tube lies outside of the outer tube and extends at an angle to the linear direction. The second element may include a grasping wire having a proximal portion and a distal portion. The grasping wire may be moveable between a grasping wire retracted position in which the distal portion of the grasping wire lies within the containment tube, and a grasping wire deployed position in which the proximal portion of the grasping wire extends substantially in the linear direction and the distal portion of the grasping wire lies outside of the containment tube and extends at an angle to the linear direction.

The distal portion of the grasping wire may have a substantially linear shape in the grasping wire retracted position. The containment tube may have a bend when in the containment tube deployed position and an aperture located at the bend. The distal portion of the grasping wire may be configured to extend through the aperture when in the grasping wire deployed position. The containment tube may have a bend when in the containment tube deployed position and a slot extending proximally from the bend. The distal portion of the grasping wire may be configured to extend through the slot when in the grasping wire deployed position. The distal portion of at least one of the grasping wire and the containment tube may have a surface that is knurled or roughened.

The device may also include an adhesive delivery tube configured to deliver an adhesive to the heart valve leaflet. The tissue securing component may be a suture having a looped portion at one end thereof. The looped portion of the suture may include a locking knot configured to slide along the suture in only one direction. The tissue securing component may be a clip. The clip may be assembled in an expanded condition around the outer tube and may be biased to contract to a clamping condition when deployed from the outer tube.

Another device for gathering tissue of a heart valve leaflet may include an outer tube extending in an elongation direction, a capture tool moveable in the outer tube between a contained position and a use position, and a tissue securing component disposed at a distal end of the outer tube and adapted to be applied to captured heart valve leaflet tissue to hold the captured tissue in a gathered configuration. The capture tool may include a needle element and a securing element. The needle element may be operable to penetrate tissue of the heart valve leaflet. The securing element may have a proximal surface adapted to capture tissue. The capture tool may be operable to draw the captured tissue into the outer tube in the gathered configuration.

The securing element may include a resorbable anchor and a suture extending from the proximal surface through the needle element. The securing element may include a barb on a distal portion of the needle element. The securing element may include an expandable element and an actuation member extending from a distal tip of the expandable element through the needle element. The expandable element may have a retracted position within the needle and a deployed position outside of the needle. The expandable element may have a substantially linear configuration with a first width in the retracted position and an expanded configuration with a second width in the deployed position. The second width may be greater than the first width.

The expandable element may be a balloon that is configured to be moved from the retracted position to the deployed position by moving the actuation member distally and inflating the balloon. The expandable element may be configured to expand from the first width to the second width by moving the actuation member proximally. The expandable element may be a wire basket. The expandable element may be a polypropylene frame. The tissue securing component may be a suture having a looped portion at one end thereof. The looped portion of the suture may include a locking knot configured to slide along the suture in only one direction. The tissue securing component may be a clip. The clip may be assembled in an expanded condition around the outer tube and may be biased to contract to a clamping condition when deployed from the outer tube.

Yet another device for gathering tissue of a heart valve leaflet may include an outer tube extending in an elongation direction, a capture tool including a grasping wire moveable relative to the outer tube in the elongation direction, and a tissue securing component disposed at a distal end of the outer tube and adapted to be applied to captured heart valve leaflet tissue to hold the captured tissue in a gathered configuration. The grasping wire may have a distal portion and proximal portion extending substantially in a linear direction and located outside of the outer tube. The grasping wire may be moveable between a grasping wire retracted position and a grasping wire deployed position in which the distal portion of the grasping wire lies outside of the outer tube and has a hook shape. The grasping wire may be operable to capture and draw tissue into the outer tube in the gathered configuration.

When the grasping wire is in the grasping wire retracted position, the distal portion of the grasping wire may lie within a containment tube operatively connected to the outer tube. When the grasping wire is in the grasping wire deployed position, the distal portion of the grasping wire may lie outside of the containment tube. When the grasping wire is in the grasping wire deployed position, the distal portion of the grasping may have a curved portion adjacent the proximal portion and a straight portion that extends in a proximal direction substantially parallel to the linear direction from the curved portion to a distal free end of the grasping wire. The straight portion may have a length of about 10 mm to about 15 mm between the curved portion and the distal free end of the grasping wire. A distal free end of the grasping wire may have an atraumatic tip. The tissue securing component may be a suture having a looped portion at one end thereof. The tissue securing component may be a clip.

A transcatheter method of gathering tissue of a heart valve leaflet may include inserting an elongated catheter assembly to a position adjacent the heart valve leaflet. The catheter assembly may include an outer tube extending in an elongation direction and a capture tool moveable in the outer tube between a contained position and a use position. The method may also include moving the capture tool from the contained position to the use position, manipulating the catheter assembly so that tissue of the heart valve leaflet is captured by the capture tool, retracting the capture tool from the use position toward the contained position to draw the captured tissue into the outer tube in a gathered configuration, and securing the captured tissue to hold the captured tissue substantially in the gathered configuration.

The capture tool may include a containment tube and a grasping wire slidably disposed within the containment tube. The grasping wire may have a proximal portion that extends substantially in a linear direction and a distal portion. The method may also include sliding the distal portion of the grasping wire out from the containment tube so that the distal portion of the grasping wire extends at an angle to the linear direction. The manipulating step may include clamping the tissue between the grasping wire and the containment tube. The manipulating step may include partially retracting a distal portion of the grasping wire so that it contacts the tissue. The method may also include applying an adhesive to a surface of the tissue through the outer tube.

The capture tool may include a needle element and a securing element. The method may also include penetrating tissue of the heart valve leaflet with the capture tool and engaging a surface of the heart valve leaflet with a proximal surface of the securing element during the retracting step. The securing element may include an expandable element and an actuation member extending from a distal tip of the expandable element through the needle element. The engaging step may include expanding the expandable element from a substantially linear configuration with a first width to an expanded configuration with a second width. The second width may be greater than the first width.

The expandable element may be a balloon. The expanding step may include moving the actuation member distally and inflating the balloon. The expandable element may be a wire basket or a polypropylene frame. The expanding step may include moving the actuation member proximally. The tissue securing component may be a suture having a looped portion at one end thereof. The looped portion may include a locking knot. The securing step may include sliding the locking knot along the suture to tighten the looped portion around the captured tissue. The tissue securing component may be a clip assembled in an expanded condition around the outer tube and biased to contact to a clamping condition. The securing step may include deploying the clip from the outer tube, whereupon the clip contracts to the clamping condition around the captured tissue.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 6 is a diagrammatic side view of the distal portion of still another embodiment of a device for transcatheter gathering of heart valve leaflet tissue;

FIG. 7 is a diagrammatic side view of the distal portion of another embodiment of a device for transcatheter gathering of heart valve leaflet tissue;

FIG. 8A is a diagrammatic side cross-sectional view of the outer tube and tissue securing component of yet another embodiment of a device for transcatheter gathering of heart valve leaflet tissue;

FIG. 8B is a plan view of the clip of FIG. 8A, shown in an open position;

FIG. 8C is a perspective view of the clip of FIG. 8A, shown in a closed position;

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
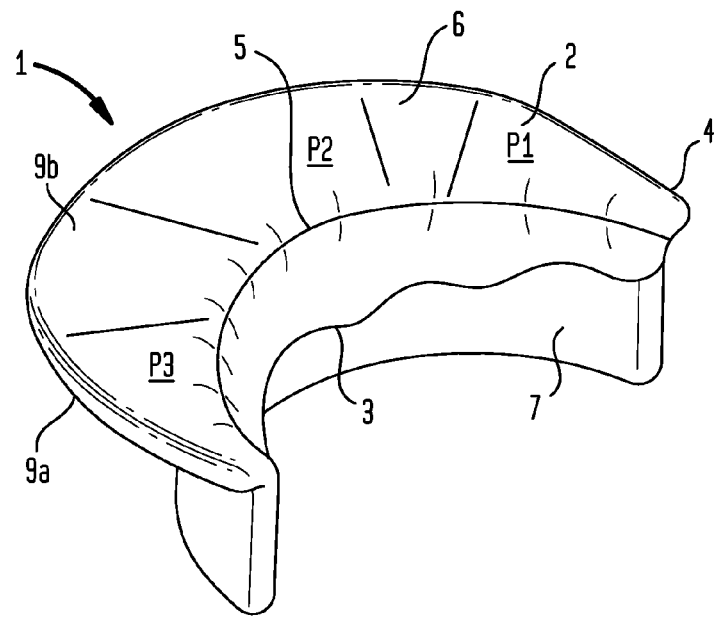
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus and the coaption line 5. Additionally, the posterior leaflet 2 has a lower portion 7 that is generally parallel to the direction of blood flow through the valve 1 and extends below the coaption line 5. The posterior leaflet 2 also has a lower surface 9a and an upper surface 9b. The posterior leaflet 2 has three scalloped portions P1, P2, and P3, any of which may include a portion that is billowed, loose, or floppy, and which therefore may be the cause of a prolapse condition of the valve. The inventive devices, systems, and methods described herein may be adapted to repair such a billowed, loose, or floppy portion of the posterior leaflet 2 or the anterior leaflet 3.

Figure 2:
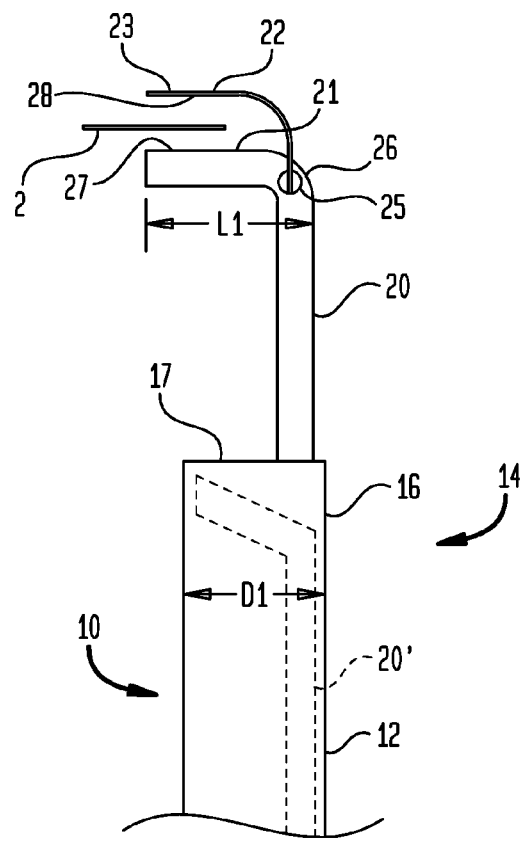
FIG. 2 is a diagrammatic side view of the distal portion of one embodiment of a device for transcatheter gathering of heart valve leaflet tissue, engaged with the posterior leaflet of the mitral valve of FIG. 1.
Figure 3:
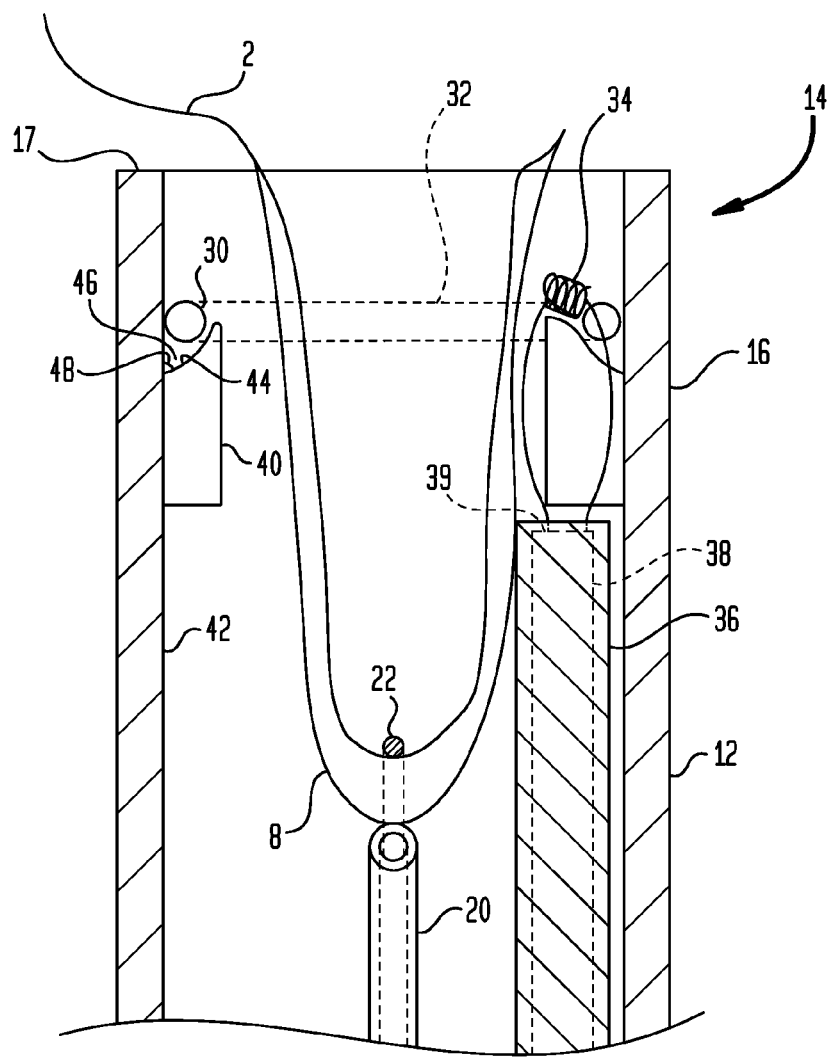
FIG. 3 is a longitudinal cross-sectional view of the outer tube and tissue securing component of the device of FIG. 2.

Referring to FIGS. 2 and 3, an exemplary device 10 for gathering of heart valve leaflet tissue includes an elongated catheter assembly 12 adapted to be inserted through the apex of a human heart so that a distal portion 14 of the catheter assembly may reach the patient's mitral valve 1 for repair thereof.

The catheter assembly 12 includes a containment tube disposed within an outer tube 16 and longitudinally slidable therein between a retracted position 20' within the outer tube and a deployed position in which a distal portion 21 of the containment tube protrudes distally beyond the open distal end 17 of the outer tube. The outer tube 16 may be made of one or more echogenic materials, so that the outer tube may be more easily visualized inside a patient using three-dimensional echocardiography.

The containment tube 20 may have an obtuse-angled shape when in the retracted position 20' within the outer tube 16, and the distal portion 21 thereof may assume a substantially right-angled shape when deployed from the outer tube. In that regard, the containment tube 20 may be formed from a memory metal or a strong, resilient metal or polymer that will cause the right-angled shape to form automatically when deployed. If the inner diameter D1 of the outer tube 16 is greater than the length L1 of the distal portion 21 of the containment tube 20, the containment tube may have a right-angled shape when fully retracted within the outer tube 16, so that the shape of the containment tube need not change when the containment tube is deployed from the outer tube. The distal portion 21 of the containment tube 20 may have an upper surface 27 that is roughened or knurled to increase the friction with a captured leaflet portion, such as the captured portion of the posterior leaflet 2.

A capture tool in the form of a grasping wire 22 is longitudinally slidable within the containment tube 20 between a retracted position substantially entirely within the lumen of the containment tube, and a deployed position in which a distal portion 23 of the grasping wire protrudes from an aperture 25 located at a bend 26 in the containment tube when the containment tube is in the deployed position. The grasping wire 22 may have a substantially linear configuration when fully retracted within the containment tube 20 and the distal portion 23 thereof may assume an L-shape when deployed from the containment tube. In that regard, the grasping wire 22 may be formed from a memory metal or a strong, resilient metal or polymer that will cause the L-shape to form automatically when deployed. The distal portion 23 of the grasping wire 22 may have a lower surface 28 that is roughened or knurled to increase the friction with a captured leaflet portion, such as the captured portion of the posterior leaflet 2.

A tissue securing component in the form of a suture loop 32 may be disposed near the open end of the outer tube 16. The suture loop 32 is formed by a length of suture 30 that extends from the proximal end of the device 10 through a suture containment tube 36 that extends longitudinally through the outer tube 16. The suture 30 exits the distal end of the suture containment tube 36 and is threaded around a rib assembly 40 extending circumferentially around and protruding radially inward from an inner surface 42 of the outer tube 16. The rib assembly 40 may be a single rib extending completely around the inner surface 42, or it may include a plurality of spaced apart ribs distributed circumferentially around the inner surface. Each rib of the rib assembly 40 has a support surface 44 that projects radially inwardly at an acute angle 48 from the inner surface 42, such that a pocket 46 is defined between the inner surface and the support surface. In any event, as the suture 30 is threaded around the rib assembly 40, it forms a loop 32 near the distal end 17 of the outer tube 16. The suture loop 32 is completed by knotting an end of the suture 30 to an intermediate portion of the suture with a locking knot 34.

The locking knot 34 is configured to slide along the suture 30 in one direction, but not the other. That is, the locking knot 34 can slide in one direction to tighten or reduce the size of the suture loop 32 when the free end of the suture 30 is pulled proximally. However, the locking knot 34 cannot slide in the opposite direction to enlarge the size of the suture loop 32. Thus, by pulling on the free or proximal end of the suture 30, the suture loop 32 is configured to move from an initial position shown in FIG. 3 to a deployed position in which the suture loop is tightened around a captured portion 8 of the posterior leaflet 2. The free or proximal end of the suture 30 is available for grasping by a user at a proximal portion of the device 10 (not shown), where it extends out from the suture containment tube 36.

A suture cutting tube 38 may be telescopically mounted within the suture containment tube 36 for sliding movement between a retracted position substantially entirely within the lumen of the suture containment tube, and a deployed position in which a distal portion of the suture cutting tube protrudes from the distal end of the suture containment tube. The suture cutting tube 38 may have a sharp distal end 39 that is configured to cut through a portion of the suture 30.

To use the device 10 to gather heart valve leaflet tissue, the suture 30 may be threaded through the suture containment tube 36, and the suture loop 32 may be fitted into the pocket 46 formed by the rib assembly 40. A slight proximal tension exerted on the free end of the suture 30 may hold the suture loop 32 in place in the pocket 46 until the suture is deployed by the user.

Next, the distal portion 14 of the catheter assembly 12 may be inserted into a patient, for example, through the apex of the heart into the left ventricle, so that the distal portion extends between the posterior leaflet 2 and the anterior leaflet 3 of the mitral valve 1. The distal end 17 of the outer tube 16 may be disposed near the coaption line 5 of the mitral valve 1, with the containment tube 20 and the grasping wire 22 positioned farthest from the posterior leaflet 2. The distal end 17 of the outer tube 16 may be guided to a position near the coaption line 5 using three-dimensional echocardiography or another imaging technique to visualize the outer tube or other components of the catheter assembly 12.

Once the outer tube 16 has been properly positioned, the containment tube 20 may be deployed by sliding the distal portion 21 thereof beyond the distal end 17 of the outer tube 16. No longer being constrained by the outer tube 16, the distal portion 21 of the containment tube 20 may assume a substantially right-angled shape, extending beneath the target portion of the posterior leaflet 2 to be captured, as shown in FIG. 2. For example, the target portion of the posterior leaflet 2 to be captured may be a loose edge of the leaflet below the coaption line 5.

The grasping wire 22 may then be deployed by sliding the distal portion 23 of the grasping wire out of the aperture 25 of the containment tube 20. No longer being constrained by the containment tube 20, the distal portion 23 of the grasping wire 22 may assume generally an L-shape that extends above the target portion of the posterior leaflet 2 to be captured.

Subsequently, the user may capture the target portion of the posterior leaflet 2 by partially retracting the grasping wire 22 until the target leaflet portion 8 is sandwiched between the lower surface 28 of the distal portion 23 of the grasping wire and the upper surface 27 of the distal portion 21 of the containment tube 20.

Referring now to FIG. 3, the user may then slide the containment tube 20 proximally to the retracted position within the outer tube 16. The proximal movement of the containment tube 20 retracts both the containment tube and the grasping wire 22, such that the captured portion 8 of the posterior leaflet 2 is pulled into the lumen of the outer tube 16 and through the suture loop 32.

Next, the user may pull the free end of the suture 30 proximally, so that the suture loop 32 will be tightened around the captured portion 8 of the posterior leaflet 2. As the suture 30 is pulled through the locking knot 34, the size of the suture loop 32 will become smaller, causing the suture loop to slide radially inwardly along the support surface 44 of the rib assembly 40 until the suture loop leaves the pocket 46 and becomes disengaged from the rib assembly. The free end of the suture 30 may be pulled proximally until the suture loop 32 is fully tightened around the captured portion 8 of the posterior leaflet 2. Because the suture 30 cannot move in a reverse direction through the locking knot 34, the suture loop 32 is held in the tightened position around the captured portion 8 of the posterior leaflet 2.

With the posterior leaflet 2 ensnared by the suture 30, the suture cutting tube 38 may be moved distally so that the distal portion thereof protrudes from the distal end of the suture containment tube 36. The suture cutting tube 38 may be moved distally until the distal end 39 thereof contacts and cuts through a portion of the suture 30 outside of the suture loop 32.

After the suture loop 32 has been adequately secured on the captured tissue 8 of the posterior leaflet 2, the device 10 may be withdrawn from the patient. As a first step, the grasping wire 22 and the containment tube 20 may be disengaged from the posterior leaflet 2 by moving the grasping wire distally to release it from contact with the posterior leaflet. Then, the grasping wire 22 may be retracted proximally into the containment tube 20, causing the grasping wire to straighten as it does so. The catheter assembly 12 may subsequently be withdrawn from the patient through the apex of the heart. The procedure described above may be repeated to apply one or more additional sutures onto the same posterior leaflet 2.

Figure 4A:
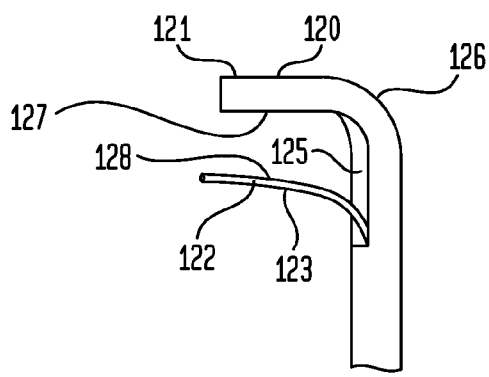
FIGS. 4A and 4B are a diagrammatic side view and a front view of the distal portion of another embodiment of a device for transcatheter gathering of heart valve leaflet tissue.
Figure 4B:
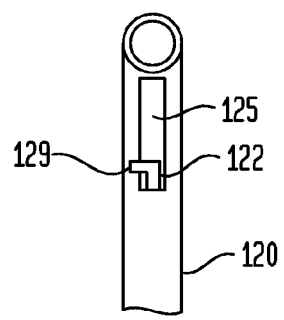

An alternative embodiment of a capture tool in the form of a grasping wire 122 that is longitudinally slidable within a containment tube 120 that is suitable for use in the device 10 is shown in FIGS. 4A and 4B. The grasping wire 122 and the containment tube 120 are similar to the grasping wire and the containment tube 20 described above, but they include an alternate arrangement. Rather than being configured to capture tissue between a lower surface of the grasping wire and an upper surface of the containment tube, the grasping wire 122 and the containment tube 120 are configured to capture tissue between a lower surface 127 of the containment tube and an upper surface 128 of the grasping wire.

The grasping wire 122 is longitudinally slidable within the containment tube 120 between a retracted position substantially entirely within the lumen of the containment tube, and a deployed position in which a distal portion 123 of the grasping wire protrudes from a slot 125 extending proximally from a bend 126 in the containment tube when the containment tube is in the deployed position. The grasping wire 122 has a laterally projecting tab 129 on its distal end that prevents the distal portion 123 of the grasping wire from being fully withdrawn into the lumen of the containment tube 120. As such, the tab 129 ensures that the distal portion 123 of the grasping wire extends through the slot 125 when deployed, rather than through the distal portion 121 of the containment tube 120.

The grasping wire 122 and the containment tube 120 may be used for transcatheter gathering of heart valve leaflet tissue in a manner similar to the grasping wire 22 and the containment tube 20 described above, except that the distal portion 121 of the containment tube 120 may be positioned above the target portion of the posterior leaflet 2 to be captured, while the distal portion 123 of the grasping wire 122 may be positioned below the target portion of the posterior leaflet to be captured. The user may capture the target portion of the posterior leaflet 2 by moving the grasping wire 122 distally until the target leaflet portion is sandwiched between the upper surface 128 of the distal portion 123 of the grasping wire and the lower surface 127 of the distal portion 121 of the containment tube 120.

Figure 5A:
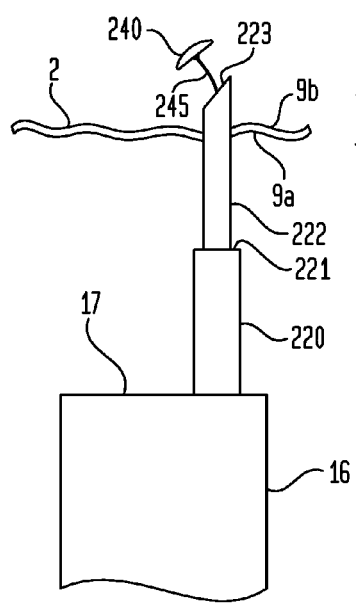
FIGS. 5A and 5B are a diagrammatic side view and an enlarged side view of the distal portion of yet another embodiment of a device for transcatheter gathering of heart valve leaflet tissue.
Figure 5B:
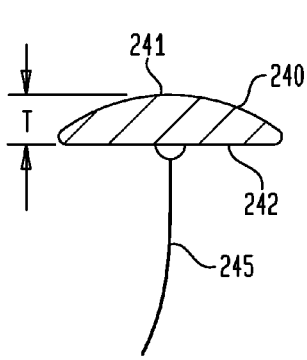

Another embodiment of a capture tool suitable for use in the device 10 is shown in FIGS. 5A and 5B. A containment tube 220 is disposed within the outer tube 16 and is longitudinally slidable therein between a retracted position within the lumen of the outer tube and a deployed position in which a distal end 221 of the containment tube protrudes distally beyond the distal end 17 of the outer tube. A needle 222 is longitudinally slidable within the containment tube 220 between a retracted position substantially entirely within the lumen of the containment tube, and a deployed position in which a tapered distal end 223 of the needle protrudes from the distal end 221 of the containment tube.

A resorbable anchor 240 has a retracted position within the needle 222 and a deployed position outside the needle. The anchor 240 may have a thickness T between its top surface 241 and bottom surface 242 that is equal to or slightly smaller than the diameter of the lumen of the needle 222. The anchor 240 may be deployed from the retracted position with the needle 222 by increasing the pressure within the needle, using pressurized saline, for example, so that an expelling force applied to the anchor is greater than the frictional forces holding the anchor in place. A suture 245 is joined to substantially the geometric center of the bottom surface 242 of the anchor 240, such that the anchor can pivot with respect to the suture. A free end of the suture 245 extends proximally through the needle 222, the containment tube 220, and the outer tube 16 to a proximal portion of the device 10 (not shown), where it may be grasped by the user.

The needle 222 and the anchor 240 may be used to capture heart valve leaflet tissue by inserting the distal portion of the catheter assembly into a patient as described above so that the distal end 17 of the outer tube 16 may be disposed near the coaption line of the mitral valve. The containment tube 220 may be deployed by sliding the distal end 221 thereof beyond the distal end 17 of the outer tube 16. The deployed containment tube 220 may be guided such that its distal end 221 contacts a lower surface 9a of the posterior leaflet 2 in a target region thereof.

Next, the needle 222 may be deployed by sliding the needle distally out of the containment tube 220, such that the tapered distal end 223 of the needle pierces the posterior leaflet 2 and extends therethrough to an upper surface 9b of the leaflet. The anchor 240 may then be deployed from the needle 222 by increasing the pressure within the needle using pressurized saline. With the anchor 240 ejected, the needle 222 may be withdrawn from the posterior leaflet 2 and retracted into the containment tube 220, leaving the anchor adjacent the upper surface 9b of the leaflet and the suture 245 extending through the opening in the leaflet created by the needle. The suture 245 may then be pulled proximally by the user until the bottom surface 242 of the anchor 240 contacts the upper surface 9b of the leaflet.

The user may then slide the containment tube 220 proximally to the retracted position within the lumen of the outer tube 16, thereby drawing the anchor 240 proximally, and with it the posterior leaflet 2, until a portion 8 of the posterior leaflet is drawn into the open end of the outer tube and through the suture loop 32. After the suture loop 32 has been adequately tightened around the captured tissue 8 of the posterior leaflet 2 as described above, the suture 245 may be detached from the anchor 240, for example, by pulling the suture proximally until it is torn from the bottom surface 242 of the anchor, or by cutting the suture using a cutting mechanism, such as the cutting tube 38 described above. The entire device may then be removed from the patient, and the anchor 240 that is left in the captured tissue of the posterior leaflet 2 may be resorbed over time.

Figure 5C:
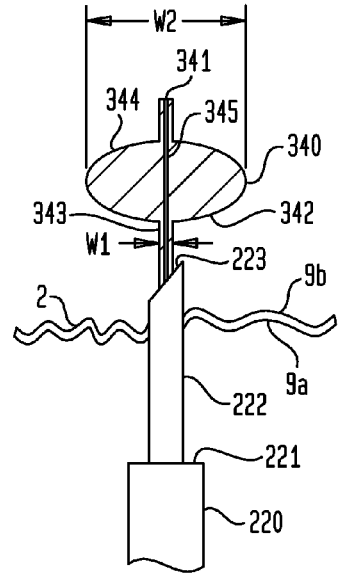
FIG. 5C is a diagrammatic side view of the distal portion of a variant of the device of FIG. 5A including a capture tool having an inflatable balloon tab.

An alternative embodiment of a capture tool in the form of a balloon 340 that is deployable from the needle 222 shown in FIG. 5A is shown in FIG. 5C. Similar to the anchor 240, the balloon 340 has a retracted position within the needle 222 and a deployed position outside of the needle. The balloon 340 may have a stem 343 having a first width W1, and a distal portion 344 that is expandable to a second width W2 greater than the first width. A rigid wire 345 may extend proximally within the balloon from a distal tip 341 of the balloon, through the outer tube 16, to a proximal portion of the device 10 (not shown), where it may be grasped by the user.

The needle 222 and the balloon 340 may be used for capturing heart valve leaflet tissue by inserting the distal portion of the catheter assembly into a patient and deploying the needle to pierce a target portion of the posterior leaflet 2 as described above with reference to the device of FIGS. 5A and 5B. Once the tapered distal end 223 of the needle 222 extends through the posterior leaflet 2, the balloon 340 may be deployed from the needle by moving the rigid wire 345 distally relative to the needle. The distal portion 344 of the balloon 340 may then be inflated, for example, using a source of pressurized helium or saline. When the balloon 340 has been inflated such that the distal portion 344 defines a lower surface 342 facing the upper surface 9b of the posterior leaflet 2, the needle 222 may be withdrawn from the posterior leaflet 2 and retracted into the containment tube 220, leaving the distal portion of the balloon adjacent the upper surface of the leaflet and the stem 343 of the balloon extending through the opening in the leaflet created by the needle. The rigid wire 345 may then be pulled proximally by the user so that the lower surface 342 of the balloon is moved into contact with the upper surface 9b of the leaflet.

The user may then slide the containment tube 220 proximally to the retracted position within the lumen of the outer tube 16, thereby pulling the balloon 340 and the posterior leaflet 2 proximally. The posterior leaflet 2 is pulled proximally until a portion 8 thereof is drawn into the open end of the outer tube 16 and through the suture loop 32. After the suture loop 32 has been adequately tightened around the captured tissue 8 of the posterior leaflet 2 as described above, the balloon 340 may be deflated to collapse the distal portion 344 thereof and may be withdrawn from the leaflet. This may be accomplished by pulling the rigid wire 345 proximally until the distal portion of the balloon passes through the leaflet and the balloon is moved back to the retracted position within the needle 222. Subsequently, the entire device may be removed from the patient.

Figure 5D:
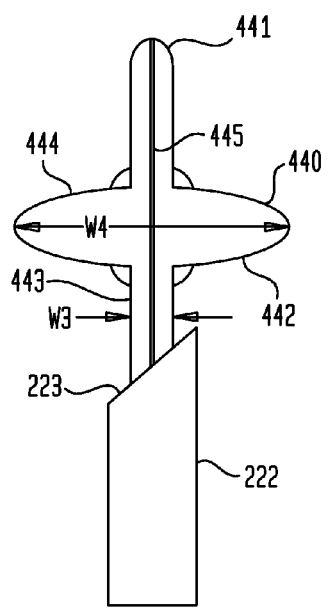
FIG. 5D is a diagrammatic side view of the distal portion of another variant of the device of FIG. 5A including a capture tool having an expandable metal tab.

Another alternative embodiment of a capture tool is shown in FIG. 5D. The capture tool of FIG. 5D includes a wire basket 440 that, similar to the balloon 340, has a retracted position within the needle 222 and a deployed position outside of the needle. The wire basket 440 may have a stem 443 that has a width W3, and a distal portion 444 that is expandable from a substantially linear configuration with a first width W3 to a second width W4 greater than the first width. The stem 443 may extend through the outer tube 16 to a proximal portion of the device 10, where it can be grasped by the user. A suture or wire 445 may extend proximally from the distal tip 441 of the wire basket, through the outer tube 16, to a free end at a proximal portion of the device 10 (not shown), where it may be grasped by the user.

The wire basket 440 may be biased to a linear configuration having the first width W3, so that the wire basket may be fully retracted within the needle 222. The wire basket 440 may have thinned or weakened portions that enable the distal portion 444 of the wire basket to be moved into a basket shape when deployed from the needle 222 and when the suture 445 is pulled proximally. In that regard, the wire basket 440 may be formed from a memory metal or a strong, resilient metal or polymer that will form the basket shape when the suture 445 is pulled proximally and that will return to the linear configuration when the suture is released. In a variant hereof, the distal portion 444 may form the basket shape automatically when deployed from the needle 222, without the need to pull on the suture 445, and the distal portion may collapse to the linear configuration as it is retracted into the needle.

The needle 222 and the wire basket 440 may be used to capture heart valve leaflet tissue by inserting the distal portion of the catheter assembly into a patient and deploying the needle to pierce a target portion of the posterior leaflet 2 as described above with reference to the device of FIGS. 5A and 5B. Once the tapered distal end 223 of needle 222 extends through the posterior leaflet 2, the wire basket 440 may be deployed from the needle by sliding the wire basket distally relative to the needle 222. When the distal portion 444 of the wire basket 440 has been ejected from the needle 222, it may be expanded by pulling the free end of the suture 445 in a proximal direction, such that the distal tip 441 of the wire basket is pulled proximally toward the needle. When the wire basket 440 has been expanded such that the distal portion 444 defines a lower surface 442 facing the upper surface 9b of the posterior leaflet 2, the needle 222 may be withdrawn from the posterior leaflet 2 and retracted into the containment tube 220, leaving the distal portion of the wire basket adjacent the upper surface of the leaflet and the stem 443 of the wire basket extending through the opening in the leaflet created by the needle. The proximal end of the wire basket 440 may then be pulled proximally by the user so that the lower surface 442 of the wire basket is moved into contact with the upper surface 9b of the leaflet.

The user may then slide the containment tube 220 proximally to the retracted position within the lumen of the outer tube 16, thereby pulling the wire basket 440 and the posterior leaflet 2 proximally. The posterior leaflet 2 is pulled proximally until a portion 8 thereof is drawn into the open end of the outer tube 16 and through the suture loop 32. After the suture loop 32 has been adequately tightened around the captured tissue 8 of the posterior leaflet 2 as described above, the suture 445 may be released, whereupon the bias of the wire basket 440 returns the distal portion 444 thereof to a linear configuration. The wire basket 440 may then be withdrawn from the leaflet by pulling the proximal end of the wire basket proximally until the distal portion of the wire basket passes through the leaflet and the wire basket is moved back to the retracted position within the needle 222. The entire device may subsequently be removed from the patient.

Figure 5E:
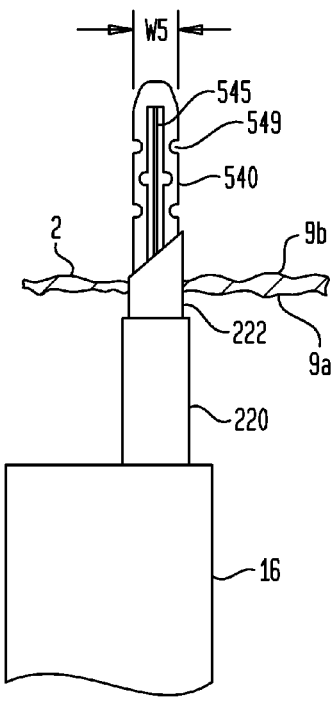
FIG. 5E is a diagrammatic side view of the distal portion of yet another variant of the device of FIG. 5A including a capture tool having an expandable plastic tab, shown with the tab in a collapsed position.
Figure 5F:
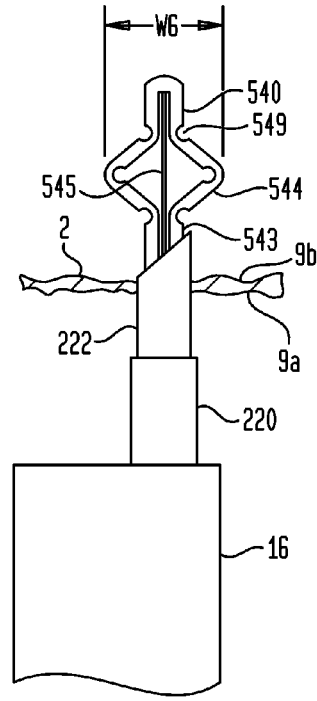
FIG. 5F is a diagrammatic side view of the distal portion the device of FIG. 5E, shown with the tab in an expanded position.

Yet another embodiment of a capture tool is shown in FIGS. 5E and 5F. The capture tool of these figures includes a polypropylene frame 540 with a similar structure and the same function as the wire basket 440 described above. The frame 540 may have a stem 543 with a width W5, and a distal portion 544 that is expandable from a substantially linear configuration with a first width W5 to a second width W6 greater than the first width. The frame 540 may have thinned or weakened portions, shown in the form of living hinges 549, which enable the distal portion 544 of the frame to be moved from the substantially linear configuration to the expanded configuration when deployed from the needle 222. A suture or wire 545 extending proximally from the distal tip 541 of the frame 540 may be pulled proximally to facilitate the movement of the frame from the substantially linear configuration to the expanded configuration. The frame 540 may be biased so that, when the suture 545 is released, the frame returns to the substantially linear configuration.

A further embodiment of a capture tool is shown in FIG. 6. The capture tool of FIG. 6 includes a needle 622 longitudinally slidable within the containment tube 220 between a retracted position substantially entirely within the lumen of the containment tube, and a deployed position in which a tapered distal end 623 of the needle protrudes from the distal end 221 of the containment tube. The needle 622 has a channel 624 extending inwardly and distally from a side thereof. The channel 624 defines a proximally-facing barb 625 at a spaced distance from the distal end 623 of the needle 622. The barb 625 may be aligned with the outer diameter of the needle 622, as shown in FIG. 6, or may protrude laterally beyond the outer diameter of the needle to make it easier for the barb to grasp leaflet tissue, such that the distal portion of the needle containing the barb would have a greater diameter than the portion of the needle proximal of the barb.

The needle 622 may be used to capture heart valve leaflet tissue by inserting the distal portion of the catheter assembly into a patient and deploying the needle to pierce a target portion of the posterior leaflet 2 as described above with reference to the device of FIGS. 5A and 5B. Once the tapered distal end 623 of the needle 622 extends through the posterior leaflet 2 sufficiently for the barb 625 to be exposed at the upper surface 9b of the leaflet, the needle 622 may be moved proximally until the barb engages into a portion of the upper surface of the leaflet.

Rather than piercing the posterior leaflet 2 with the needle 622, the needle may be placed between the posterior and anterior leaflets, and the needle may be deployed distally so that the barb 625 is located distally of the upper surface 9b of the leaflet and faces toward the posterior side of the annulus. The needle 622 may then be moved proximally until the barb engages into a portion of the upper surface 9b of the leaflet 2. In a design wherein the needle 622 is not intended to pierce the leaflet 2, the distal end of the needle may be rounded to avoid cutting or piercing of the leaflet as the needle is deployed distally.

With the barb 625 of the needle 622 engaged in the upper surface of the leaflet 2, the user may slide the containment tube 220 proximally to the retracted position within the lumen of the outer tube 16, thereby pulling the needle and the posterior leaflet proximally until a captured portion of the posterior leaflet is pulled into the outer tube and through the suture loop 32. After the suture loop 32 has been adequately tightened around the captured tissue 8 of the posterior leaflet 2 as described above, the needle 622 may be disengaged from the leaflet by further retracting the containment tube 220 until the barb 625 tears through the leaflet, allowing the distal end 623 of the needle 622 to pass back through the leaflet and into the retracted position in the containment tube. The entire device may then be removed from the patient.

Yet another embodiment of a capture tool is shown in FIG. 7. The capture tool of FIG. 7 is in the form of a grasping wire 722 that is deployable from the containment tube 220 shown in FIG. 5A. The grasping wire 722 is longitudinally slidable within the containment tube 220 between a retracted position substantially entirely within the lumen of the containment tube, and a deployed position in which a distal portion 723 of the grasping wire protrudes from the distal end 221 of the containment tube. Similar to the grasping wire 22 shown in FIG. 2, the grasping wire 722 may have a linear configuration when fully retracted within the containment tube 220, and the distal portion 723 thereof may assume an L-shape when deployed from the containment tube. The distal portion 723 of the grasping wire 722 may have a lower surface 728 that is roughened or knurled to increase the friction with a captured posterior leaflet portion.

The containment tube 220 may also include a delivery tube 740 extending therein from the distal end 221 of the containment tube to a location at a proximal end of the device 10. The delivery tube 740 may be configured to deliver a bioadhesive 745 to the distal end 221 of the containment tube 220 for application to the posterior leaflet 2. The distal end of the delivery tube 740 may be sealed with a septum or other structure to prevent the bioadhesive from curing before it is exposed to leaflet tissue. The septum or other structure may be ruptured at the proper time to enable the bioadhesive 745 to be dispensed from the delivery tube 740.

The grasping wire 722 and the bioadhesive 745 may be used for capturing heart valve leaflet tissue by inserting the distal portion of the catheter assembly into a patient, deploying the containment tube 220 from the outer tube 16, and deploying the grasping wire from the containment tube so that the distal portion 723 thereof assumes an L-shape. The grasping wire 722 and the containment tube 220 may then be positioned so that the distal portion 723 of the grasping wire lies above the portion of the posterior leaflet 2 to be captured, and the distal end 221 of the containment tube, and therefore the distal end of the delivery tube 740, lies below the target portion of the leaflet.

The user may then capture the target portion of the posterior leaflet 2 by retracting the grasping wire 722 proximally within the containment tube 220 until a portion of the posterior leaflet 2 is sandwiched between the grasping wire and the distal end 221 of the containment tube. The bioadhesive 745 may then be expelled from the delivery tube 740 onto the lower surface 9a of the posterior leaflet 2, for example, by inserting pressurized saline into the proximal end of the delivery tube, activating a plunger, or the like. After a few seconds, the bioadhesive 745 may be cured, thereby temporarily affixing the captured leaflet tissue to the distal end of the delivery tube 740.

With the bioadhesive 745 applied to the posterior leaflet 2, the user may slide the containment tube 220 proximally to the retracted position within the lumen of the outer tube 16, pulling a captured portion 8 of the posterior leaflet 2 into the outer tube 16 and through the suture loop 32. After the suture loop 32 has been adequately tightened around the captured tissue 8 of the posterior leaflet 2 as described above, the delivery tube 740 may be disengaged from the leaflet, for example, by rotating the delivery tube about its longitudinal axis until the delivery tube detaches from the lower surface 9a of the posterior leaflet. Such detachment can be made easier if the bioadhesive 745 is selected to be weaker in shear than in tension, such that the posterior leaflet 2 does not detach from the delivery tube 740 until the rotation of the delivery tube applies sufficient shearing force to the leaflet. The grasping wire 722 may then be retracted into the containment tube 220, and the entire device may be removed from the patient.

In a variant of the embodiment described with reference to FIG. 7, the delivery tube 740 may be omitted, and the bioadhesive 745 may be expelled onto the upper surface 9b of the posterior leaflet 2 from an opening in the lower surface 728 of the distal portion 723 of the grasping wire 722. In another variant, the delivery tube 740 may be omitted, and the bioadhesive 745 may be expelled onto the lower surface 9a of the posterior leaflet 2 from an opening in the upper surface 727 of the distal portion 723 of the grasping wire 722. In yet another variant, the containment tube 220 may also have a vacuum tube disposed adjacent the delivery tube 740. While the target portion of the posterior leaflet 2 is being sandwiched between the grasping wire 722 and the distal end 221 of the containment tube 220, the distal end of such vacuum tube can be disposed adjacent the lower surface 9a of the posterior leaflet, and a vacuum can be applied to pull the leaflet more tightly against the distal end of the containment tube for application of the bioadhesive 745 to the leaflet.

FIGS. 8A-8C show an alternative embodiment of a tissue securing component in the form of a clip 830 that is configured to be applied around a captured portion 8 of the posterior leaflet 2. The clip 830 may be used in place of the suture 30 and suture loop 32 described above. The clip 830 may be made of a memory metal and may be biased to curl into a substantially round configuration (FIG. 8C) when deployed from the outer tube 16. A prong 832 at each end of the clip 830 may be configured to become embedded in the leaflet tissue when the clip is deployed. One or more clips 830 may be disposed in an open configuration around the outer surface 19 of the outer tube 16 adjacent the distal end 17 thereof. The outer tube 16 may be slidably disposed in a deployment tube 850 with a tight clearance, such that the clip 830 will interfere with the distal end 852 of the deployment tube as the deployment tube is moved toward the distal end 17 of the outer tube.

The clip 830 and the deployment tube 850 may be used to secure heart valve leaflet tissue by first inserting the distal portion of the device 810 into a patient, and then deploying any one of the tissue capturing embodiments described above to capture a portion of the posterior leaflet within the outer tube 16. The user may then push the deployment tube 850 distally until the distal end 852 thereof contacts the clip 830 and pushes it in a distal direction off of the distal end 17 of the outer tube 16. As the clip 830 is released from the outer tube 16, it will collapse to a substantially round configuration according to its bias, and the two prongs 832 of the clip will become embedded in the captured tissue 8 of the posterior leaflet 2, thereby securing the tissue. If a plurality of clips 830 are disposed adjacent one another at the distal end 17 of the outer tube 16, additional clips can be deployed onto the posterior leaflet 2 by continuing to move the deployment tube 850 distally until each additional clip is pushed off of the outer tube as desired.

Figure 9A:
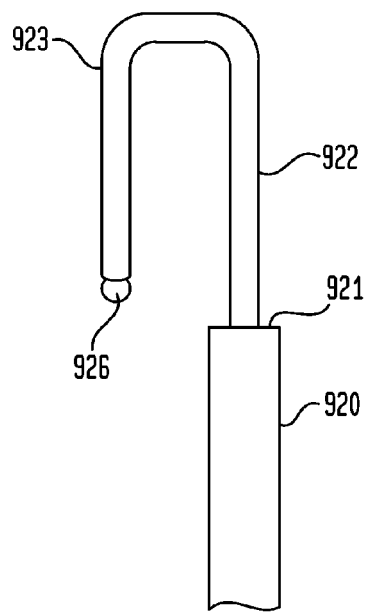
FIG. 9A is a diagrammatic side view of the distal portion of a hook for acting on heart valve leaflet tissue.
Figure 9B:
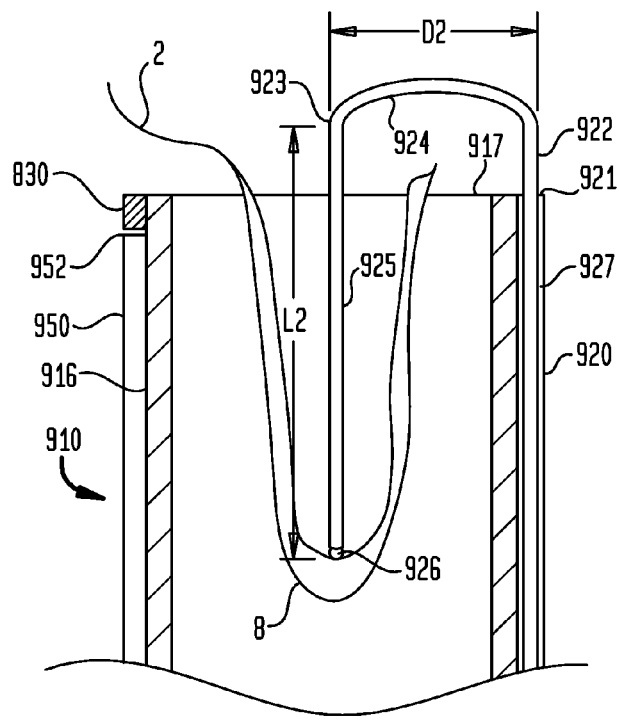
FIG. 9B is a diagrammatic side cross-sectional view of the outer tube and tissue securing component of another embodiment of a device for transcatheter gathering of heart valve leaflet tissue, shown with the hook of FIG. 9A.
Figure 9C:
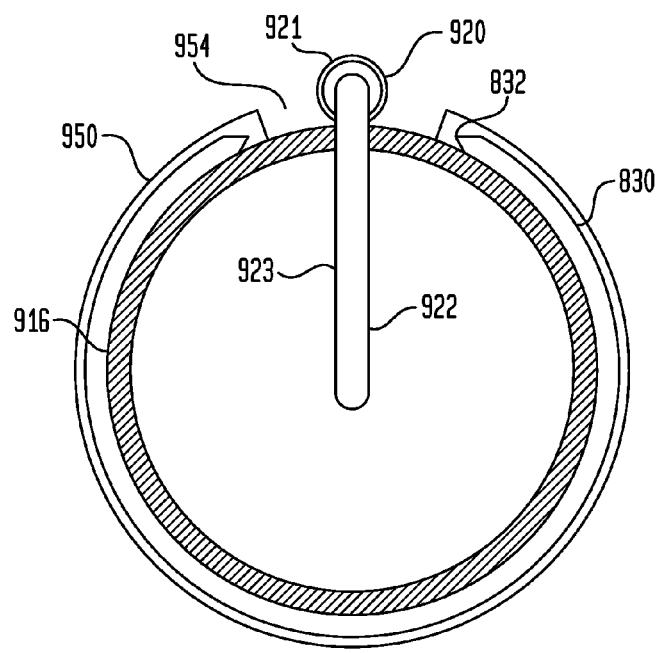
FIG. 9C is a top view of the apparatus of FIG. 9B.

An alternative embodiment of a capture tool suitable for use in a device 910 similar to the device 810 of FIG. 8A is shown in FIGS. 9A-9C. The capture tool includes a grasping wire 922 that is longitudinally slidable within a containment tube 920 between a retracted position in which a distal portion 923 of the grasping wire is substantially entirely within the lumen of the containment tube, and a deployed position in which the distal portion of the grasping wire protrudes from the distal end 921 of the containment tube. At its proximal end, the grasping wire 922 may extend to a handle (not shown) of the device 910, at which it may be operated by a user of the device.

The grasping wire 922 may have a substantially linear configuration when fully retracted within the containment tube 920, and the distal portion 923 thereof may assume a hook shape when deployed from the containment tube, while the proximal portion 927 thereof remains in the substantially linear configuration. In that regard, the grasping wire 922 may be formed from a shape memory material, such as a memory metal or a strong, resilient metal or polymer that will cause the hook to form automatically when deployed. The distal free end of the grasping wire 922 may have an atraumatic tip 926 to help prevent the grasping wire from piercing or tearing the leaflet tissue. The atraumatic tip 926 may be a ball-shaped element formed on or attached to the distal free end of the grasping wire 922, as shown in FIGS. 9A and 9B. Alternatively, the atraumatic tip 926 may be a coiled portion of the distal portion 923 of the grasping wire.

When the distal portion 923 of the grasping wire 922 is deployed from the containment tube 920 and assumes a hook shape, the distal portion may include a curved portion 924 adjacent the proximal portion and a straight portion 925 that extends in a proximal direction from the curved portion to the distal free end of the grasping wire. The straight portion 925 may have a length L2 between the curved portion 924 and the distal free end of the grasping wire. L2 may be any length, depending on how much tissue is desired to be captured and secured, including, for example, about 10 mm to about 15 mm. The straight portion 925 of the grasping wire may be oriented substantially parallel to the proximal portion 927, as shown in FIG. 9B. Alternatively, the straight portion 925 of the grasping wire may be oriented at an acute angle relative to the proximal portion 927. The curved portion 924 may extend from the proximal portion 927 across a lateral distance D2 approximately equal to the radius of the outer tube 916, so that when the straight portion 925 is inserted into the outer tube, the distal free end of the grasping wire may be located at or close to the longitudinal axis of the outer tube.

The device 910 has an outer tube 916 that is the same as the outer tube 16 shown in FIG. 3. The containment tube 920 extends along the outside surface of the outer tube 916 between the distal end 917 of the outer tube and a handle (not shown) at a proximal end of the device 910. Alternatively, the containment tube 920 may extend along the outside surface of the outer tube 916 between the distal end 917 of the outer tube and an aperture (not shown) extending through the outer tube. A proximal portion of the grasping wire 922 may extend within the outer tube 916 between the aperture and a handle at a proximal end of the device 910. In embodiments having such an aperture configured to receive a proximal portion of the grasping wire 922, the containment tube 920 may have a length that is sufficient for the distal portion 923 of the grasping wire to be entirely retracted therein in a linear shape.

The device 910 may be used to deploy one or more of the same clips 830 as are deployed by device 810, except that the clips 830 may be assembled on the outer tube 916 of the device 910 so that the prongs 852 of the clips are located on opposite sides of the containment tube 920. In this manner, the containment tube 920 will not interfere with the movement of the clips 830 along the outer tube 816 or the deployment of the clips therefrom. The outer tube 916 may be slidably disposed in a deployment tube 950 with a tight clearance, such that the clips 830 will interfere with the distal end 952 of the deployment tube as the deployment tube is moved toward the distal end 917 of the outer tube. The deployment tube 950 may have a longitudinal slot 954 or opening extending proximally from the distal end 952 thereof for accommodating the containment tube 920.

The device 910 may be used to secure heart valve leaflet tissue, such as tissue of the posterior leaflet 2, by first inserting the distal portion of the catheter assembly into a patient, so that the distal end 917 of the outer tube 916 is disposed near the coaption line 5 of the mitral valve 1, with the containment tube 920 and the grasping wire 22 positioned farthest from the posterior leaflet.

Once the outer tube 916 has been properly positioned, the grasping wire 922 may be deployed by operating the proximal end thereof to slide the distal portion 923 out of the distal end 921 of the containment tube 920. No longer being constrained by the containment tube 920, the distal portion 923 of the grasping wire 922 may assume a hook shape that extends above the target portion of the posterior leaflet to be captured. Subsequently, the user may capture the target portion of the posterior leaflet 2 by partially retracting the grasping wire 922 until the target leaflet portion 8 is pushed into the outer tube 916, as shown in FIG. 9B.

The deployment tube 950 and one or more of the clips 830 may be used to secure the captured heart valve leaflet tissue in the same manner as described above with respect to the use of clips with the device 810. Alternatively, the suture loop 32 shown in FIG. 3 may be used in place of the clips 830 to secure heart valve leaflet tissue that has been captured by the grasping wire 922. Once the captured tissue has been secured, the grasping wire 922 may be retracted into the containment tube 920, and the entire device 910 may be removed from the patient.

Although the distal portion 923 of the grasping wire 922 is described above as assuming a hook shape only when deployed from the containment tube 920, the distal portion of the grasping wire may alternatively be made from a non-shape memory material, and such a distal portion may have an initial configuration located outside of the containment tube and having a hook shape, such that most of the straight portion 925 is initially disposed inside of the outer tube 916 as shown in FIG. 9B. In this variant, the distal portion 923 of the grasping wire 922 can be deployed by sliding the proximal portion 927 of the grasping wire out of the containment tube 920 until the distal portion extends above the target portion of the posterior leaflet 2 to be captured. The user may subsequently capture the target portion of the posterior leaflet by partially retracting the grasping wire until the target leaflet portion 8 is pushed into the outer tube 916. One or more of the clips 830 may be deployed from the outer tube 916 to secure the captured leaflet portion 8 as described above.

In the foregoing, particular structures have been described that are adapted to gather, secure, and repair heart valve leaflet tissue. The invention also contemplates the use of any alternative structures for such purposes, including structures having different lengths, shapes, and configurations.

Although the various gathering devices have been described herein in connection with tightening the posterior leaflet of a mitral valve, all of these devices may be used on other heart valve leaflets, such as the anterior leaflet of the mitral valve, or on any other tissue of the body for which a reduction in the length of the tissue would be beneficial.

Although the invention herein has been described with reference to particular embodiments in which the catheter assembly is inserted into the patient through the apex of the heart (i.e., transapical insertion), it is to be understood that the invention contemplates embodiments in which the catheter assembly extends through a portion of the vasculature of the patient to reach the heart, for example, through a transfemoral or subclavian artery, or using a transseptal procedure. Any other percutaneous technique for accessing the interior of the heart may also be used. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

INDUSTRIAL APPLICABILITY

The present invention enjoys wide industrial applicability including, but not limited to, methods and devices for gathering tissue in a patient.

The invention claimed is:

1. A device for gathering tissue of a heart valve leaflet, the device comprising:
an outer tube extending in an elongation direction;
a capture tool moveable in the outer tube between a contained position and a use position, the capture tool including a first element and a second element that are moveable relative to one another in the elongation direction, the first and second elements being operable to capture tissue of the heart valve leaflet therebetween and to draw the captured tissue into the outer tube in a gathered configuration; and
a tissue securing component disposed at a distal end of the outer tube and adapted to be applied to the captured tissue to hold the captured tissue in the gathered configuration, the tissue securing component being a suture having a looped portion at one end thereof,
wherein the second element is moveable between a retracted position in which a distal portion of the second element lies within a lumen of the first element, and a deployed position in which the distal portion of the second element lies outside of the lumen of the first element.

2. The device as claimed in claim 1, wherein the first element includes a containment tube having a proximal portion and a distal portion, the containment tube being moveable between a containment tube retracted position in which the distal portion of the containment tube lies within the outer tube, and a containment tube deployed position in which the proximal portion of the containment tube extends substantially in a linear direction and the distal portion of the containment tube lies outside of the outer tube and extends at an angle to the linear direction.

3. The device as claimed in claim 1, further comprising an adhesive delivery tube configured to deliver an adhesive to the heart valve leaflet.

4. The device as claimed in claim 1, wherein the looped portion of the suture includes a locking knot configured to slide along the suture in only one direction.

5. A device for gathering tissue of a heart valve leaflet, comprising:
an outer tube extending in an elongation direction;
a capture tool moveable in the outer tube between a contained position and a use position, the capture tool including a first element and a second element that are moveable relative to one another in the elongation direction, the first and second elements being operable to capture tissue of the heart valve leaflet therebetween and to draw the captured tissue into the outer tube in a gathered configuration; and
a tissue securing component disposed at a distal end of the outer tube and adapted to be applied to the captured tissue to hold the captured tissue in the gathered configuration,
wherein the first element includes a containment tube having a proximal portion and a distal portion, the containment tube being moveable between a containment tube retracted position in which the distal portion of the containment tube lies within the outer tube, and a containment tube deployed position in which the proximal portion of the containment tube extends substantially in a linear direction and the distal portion of the containment tube lies outside of the outer tube and extends at a first angle to the linear direction, and
wherein the second element includes a grasping wire having a proximal portion and a distal portion, the grasping wire being moveable between a grasping wire retracted position in which the distal portion of the grasping wire lies within the containment tube, and a grasping wire deployed position in which the proximal portion of the grasping wire extends substantially in the linear direction and the distal portion of the grasping wire lies outside of the containment tube and extends at a second angle to the linear direction.

6. The device as claimed in claim 5, wherein the distal portion of the grasping wire has a substantially linear shape in the grasping wire retracted position.

7. The device as claimed in claim 5, wherein the containment tube has a bend when in the containment tube deployed position and an aperture located at the bend, and the distal portion of the grasping wire is configured to extend through the aperture when in the grasping wire deployed position.

8. The device as claimed in claim 5, wherein the containment tube has a bend when in the containment tube deployed position and a slot extending proximally from the bend, and the distal portion of the grasping wire is configured to extend through the slot when in the grasping wire deployed position.

9. The device as claimed in claim 5, wherein the distal portion of at least one of the grasping wire and the containment tube has a surface that is knurled or roughened.

10. The device as claimed in claim 5, wherein the tissue securing component is a suture having a looped portion at one end thereof.

11. The device as claimed in claim 10, wherein the looped portion of the suture includes a locking knot configured to slide along the suture in only one direction.

12. The device as claimed in claim 5, wherein the tissue securing component is a clip.

13. The device as claimed in claim 12, wherein the clip is assembled in an expanded condition around the outer tube and is biased to contract to a clamping condition when deployed from the outer tube.

14. The device as claimed in claim 5, further comprising an adhesive delivery tube configured to deliver an adhesive to the heart valve leaflet.

\* \* \* \* \*